United States Patent [19]

Albrecht et al.

[11] 4,289,777
[45] Sep. 15, 1981

[54] QUINOLONECARBOXYLIC ACID DERIVATIVES AND PHARMACEUTICAL PREPARATIONS THEREOF FOR TREATMENT OF AN ALLERGIC DISEASE OF THE RESPIRATORY TRACT

[75] Inventors: Rudolf Albrecht; Eberhard Schröder; Irmgard Böttcher, all of Berlin, Fed. Rep. of Germany

[73] Assignee: Schering, Aktiengesellschaft, Berlin and Bergkamen, Fed. Rep. of Germany

[21] Appl. No.: 107,676

[22] Filed: Dec. 27, 1979

[30] Foreign Application Priority Data

Dec. 28, 1978 [DE] Fed. Rep. of Germany ....... 2856908

[51] Int. Cl.³ .................. A61K 31/47; C07D 401/12
[52] U.S. Cl. .................................. 424/258; 546/156; 560/44; 568/586
[58] Field of Search ................... 546/156; 424/258

[56] References Cited

U.S. PATENT DOCUMENTS 3,463,779 8/1969 Bowie .................................. 260/287
4,117,136 9/1978 Hisada ................................. 424/258

FOREIGN PATENT DOCUMENTS 2145423 3/1972 Fed. Rep. of Germany ...... 546/156

OTHER PUBLICATIONS

J. Med. Chem., 15:583, (1972).

Primary Examiner—Donald G. Daus
Assistant Examiner—Diana G. Rivers
Attorney, Agent, or Firm—Millen & White

[57] ABSTRACT

Quinolonecarboxylic acid derivatives of the formula

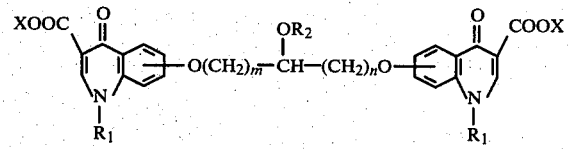

wherein
the grouping

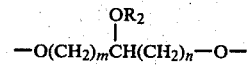

is independently in the 6-, 7- or 8-position of each of the quinolone residues;
m and n independently are each 1–4;
$R_1$ is hydrogen or alkyl of 1–6 carbon atoms;
$R_2$ is hyrogen, alkanoyl of 1–8 carbon atoms or benzoyl; and
X is hydrogen, alkyl of 1–6 carbon atoms or the cation of a base which produces a physiologically acceptable salt with the quinolonecarboxylic acid,
have valuable pharmacological properties.

15 Claims, No Drawings

QUINOLONECARBOXYLIC ACID DERIVATIVES AND PHARMACEUTICAL PREPARATIONS THEREOF FOR TREATMENT OF AN ALLERGIC DISEASE OF THE RESPIRATORY TRACT

BACKGROUND OF THE INVENTION

The present invention relates to novel quinolonecarboxylic acid derivatives, a process for their production and pharmaceutical preparations thereof.

It is known that, upon inhalation, pharmaceutical preparations containing an active ingredient of the sodium salt of cromoglycic acid, inhibit the liberation of mediators triggering bronchoconstriction, such as histamine and SRS-A, from the mast cells of the lungs. Accordingly, via prophylactic application, they are highly suitable for the treatment of allergic asthma (J. Med. Chem. 15: 583 [1972]). However, it is desirable to have such inhalants which also have other beneficial pharmacological effects at the same time.

SUMMARY OF THE INVENTION

Accordingly, it is an object of this invention to provide new pharmacologically effective agents which are not only effective to treat allergic asthma but which also simultaneously possess effectiveness in treating other indications including those which often accompany asthma.

Upon further study of the specification and appended claims, further objects and advantages of this invention will become apparent to those skilled in the art.

These objects have been attained by providing quinolonecarboxylic acid derivatives of formula I

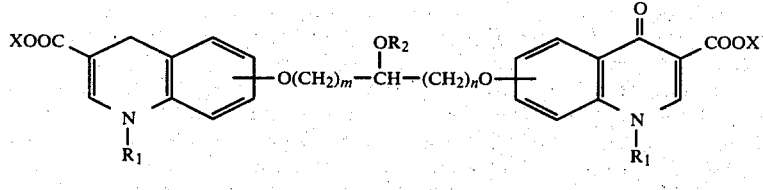

wherein
the grouping

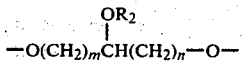

is independently in the 6-, 7- or 8-position of each of the quinolone residues;
m and n independently are ach 1–4;
$R_1$ is hydrogen or alkyl of 1–6 carbon atoms;
$R_2$ is hydrogen or acyl of 1–8 carbon atoms; and
X is hydrogen, alkyl of 1–6 carbon atoms, or the cation of a base which produces a physiologically acceptable salt with the quinolonecarboxylic acid.

DETAILED DISCUSSION

The quinolonecarboxylic acid derivatives of this invention possess the same property mentioned for the sodium salt of cromoglycic acid. However, compared with that compound, they are significantly advantageous in that they also display anti-inflammatory and antibacterial activity, both of which are favorable activities for asthma therapy.

In the quinolonecarboxylic acid derivatives of this invention, $R_1$ or X may be an alkyl group of 1–6 carbon atoms or especially of 1–4 carbon atoms, e.g., methyl, ethyl, propyl, isopropyl, butyl, isobutyl, tert-butyl, pentyl, hexyl and the like.

$R_2$ can be an acyl group of 1–8 carbon atoms or especially of 1–5 carbon atoms, such as alkanoyl, benzoyl and equivalents thereof. Alkanoyl and benzoyl are preferred. Suitable alkanoyl groups include, for example, formyl, acetyl, propionyl, butyryl and octanoyl.

In order to increase the water solubility of the quinolonecarboxylic acid derivatives of this invention, it is possible to convert the quinolonecarboxylic acid derivatives of formula I wherein X is hydrogen into the salts thereof with physiologically acceptable bases. Suitable salts include, for example, the alkali metal salts (preferably lithium salts, sodium salts or potassium salts); the alkaline earth metal salts (preferably magnesium salts or calcium salts); copper(II) salts; ammonium salts; and salts of organic amines (e.g., triethanolamine, piperazine, N-methylglucamine, etc.).

While the bridging group may independently be connected to the 6-, 7- or 8-positions of each of the two quinolone groups, bis derivatives are preferred.

m and n preferably are each 1; $R_2$ is preferably H and X is preferably hydrogen, an alkali metal cation, an alkaline earth metal cation, ammonium, piperazinyl or N-methylglucamine.

The quinolonecarboxylic acid derivatives of this invention can be prepared by:

(a) condensing a diamine of formula II

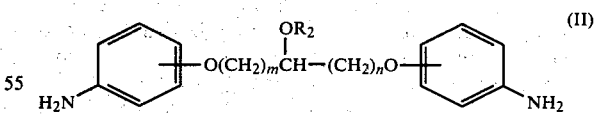

wherein m, n, and $R_2$ are as defined above, with a malonic acid derivative of formula III

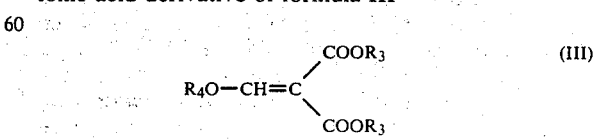

wherein $R_3$ and $R_4$ are each alkyl of 1–6 carbon atoms; and cyclizing the thus-obtained compound of formula IV

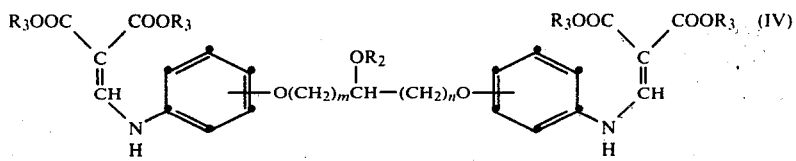

wherein m, n, $R_2$ and $R_3$ are as defined above; or (b) condensing a hydroxyquinolonecarboxylic acid derivative of formula V

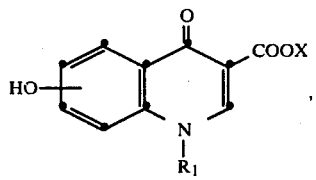

wherein
X and $R_1$ are as defined above and
the HO-group is in the 6-, 7- or 8-position of the quinolone nucleus,
with a compound of formula VI or VII

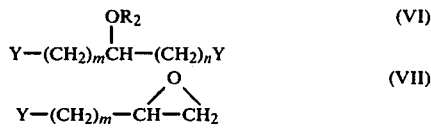

wherein
m, n and $R_2$ are as defined above and
Y is chlorine, bromine, iodine, mesylate or tosylate; and optionally subjecting the quinolonecarboxylic acid derivatives obtained according to processes (a) or (b) to saponification, esterification, N-alkylation or conversion into the salts thereof with physiologically acceptable bases.

Process (a) is conducted in a conventional manner as described, for example, in Jucker [Ed], "Fortschritte Arzneimittelforschung" [Process in Drug Research] 21:1 et seq. [1977]. The diamines of formula II can be reacted, for example, with the malonic acid derivatives of formula III, yielding the compounds of formula IV. The presence of catalyst or solvents is unnecessary for this reaction, but it is, of course, also possible to conduct this reaction in the presence of additional solvents, e.g., chlorinated hydrocarbons (methylene chloride, chloroform, tetrachloroethane, etc.), ethers (diisopropyl ether, dibutyl ether, dioxane, tetrahydrofuran, etc.), or dipolar aprotic solvents (dimethylformamide, hexamethylphosphoric triamide, etc.). This reaction step is preferably accomplished at a reaction temperature of 20°–150° C.

The cyclization of the compounds of formula IV following this process step is carried out thermally, preferably in the presence of high-boiling solvents (e.g., mineral oil, diphenyl, diphenyl ether, or "Dowtherm A") at 200°–350° C. During this reaction, the reaction temperature can be lowered to about 50°–200° C., if, additionally, a Lewis acid (acetic acid, sulfuric acid, polyphosphoric acid, boron trifluoride, phosphorus oxychloride, phosphorus trichloride, phosphorus pentachloride, aluminum chloride, zinc chloride, etc.) is introduced as a catalyst into the reaction mixture.

In process (b), the hydroxyquinolonecarboxylic acid derivatives of formula V are condensed with the compounds of formula VI or VII in inert solvents and in the presence of basic catalysts. This reaction is preferably conducted with those hydroxyquinolonecarboxylic acid derivatives of formula V wherein the substituents $R_1$ is alkyl. Suitable basic catalysts for this reaction include, for example, alkali metal bicarbonates (sodium bicarbonate, potassium bicarbonate), alkali carbonates (sodium carbonate, potassium carbonate), alkali metal hydroxides (sodium hydroxide, potassium hydroxide) or alkali metal alcoholates (sodium methylate, sodium ethylate, potassium methylate, potassium tert-butylate, etc.). Suitable solvents include, for example, lower alcohols (especially those of 1-4 carbon atoms, such as methanol, ethanol, propanol, isopropanol or tert-butanol), polar ethers (dioxane, tetrahydrofuran, glycol dimethyl ether, glycol monomethyl ether, etc.) or dipolar aprotic solvents (such as dimethylformamide, N-methylacetamide, dimethyl sulfoxide or hexamethylphosphoric triamide). Typical temperatures are 0°–200° C.

The optionally subsequent saponification of the esters can be conducted according to conventional operating methods. For example, the esters can be saponified in water or aqueous alcohols in the presence of acidic catalysts, such as hydrochloric acid, sulfuric acid, p-toluenesulfonic acid, or in the presence of basic catalysts, such as potassium bicarbonate, potassium carbonate, sodium hydroxide or potassium hydroxide.

The optional subsequent alkylation of any secondary amino groups likewise can be conducted in accordance with methods known per se for conventional N-alkylation of quinolone derivatives.

Thus, it is possible, for example, to metallize the nitrogen atoms of the compounds by reaction with metal hydrides or metal amides—such as sodium hydride or sodium amide—and treat the thus-obtained reactive compounds with the sulfates or halogenides (chlorides, bromides, or iodides) of the finally desired hydrocarbon residue. Polar aprotic solvents, such as dimethylformamide, N-methylpyrrolidone or hexamethylphosphoric triamide, are preferably employed for this reaction, which latter is effected at a reaction temperature of about 0°–120° C.

The optional subsequent esterification of the free hydroxymethyl group is likewise conducted according to operating methods known for this purpose. One possible esterification route is, for example, the esterification of the hydroxy compounds with acid anhydrides or acid chlorides in the presence of aromatic N-heterocycles, such as pyridine, collidine or lutidine, or in the presence of aqueous solutions of basic alkali metal carbonate, e.g., sodium bicarbonate, potassium bicarbonate, sodium carbonate, sodium hydroxide or potassium hydroxide.

The optional subsequent conversion of the quinolonecarboxylic acid derivatives into the salts thereof, also can be conducted under conditions well-known to those skilled in the art, by neutralizing these compounds with a physiologically acceptable base.

The starting compounds for the processes of this invention are known or can be prepared by fully conventional techniques. Typical preparation methods for these starting compounds are described below with reference to several typical compounds. (See A-E below.)

As noted above, the quinolonecarboxylic acid derivatives of this invention are distinguished by antiallergic, antiinflammatory and antibacterial activity.

To demonstrate the antiallergic activity, it is possible to measure the inhibition of mediator liberation by using the model of passive cutaneous anaphylaxis in rats (PCA) (Ovary, Z.: Immunological Methods, ed. J. F. Ackroyd, Blackwell Scientific Publ. Oxford: 259 [1964]). For this purpose, rats are passively sensitized by the intracutaneous injection of various dilutions (1:8 and 1:16) of a standardized IgE-containing hyperimmune serum. After 48 hours, the compound to be tested, dissolved as the sodium salt in a physiological NaCl solution, and ovalbumin as the allergen, combined with a dye to better measure the local allergic reaction, are administered intravenously.

The measurement determines the inhibition of the allergic reaction in the presence of the test compound as compared with the allergic reaction without the inhibiting agent. Thus-obtained values for several compounds of this invention are indicated in Table 1. As can be seen, there is at least an equivalence between the effectiveness of the compounds of this invention and that of cromoglycic acid.

The inflammation-inhibitory effect can be measured by the carrageenin test (Winter, C. A., E. A. Risley and G. W. Nuss, Proc. Soc. Exp. Biol. Med. 111: 544–547 [1962]). Such results are shown in Table 2. As can be seen from the table, the compounds of this invention show a marked antiinflammatory activity, whereas the cromoglycic acid shows only an extremely weak efficacy, or even no corresponding efficacy at all.

The antibacterial effect can be measured in vitro in a series dilution test. The results for several compounds are shown in Table 3. As can be seen therefrom, the compounds of this invention exhibit antibacterial activity against *Diplococcus pneumoniae* and a series of strains of *Staphylococcus aureus*, whereas cromoglycic acid is ineffective against all bacteria investigated.

TABLE 1

Antiallergic Effect, Shown In the Rat PCA Test Upon i.v. Application

| Compound | Dosage mg./kg. | % Inhibition IgE 1:8 | % Inhibition IgE 1:16 |
|---|---|---|---|
| 1,3-Bis(1-ethyl-3-carboxy-1,4-dihydro-4-oxo-7-quinolyloxy)-2-propanol | 10 | 84 | 90 |
|  | 5 | 59 | 69 |
| 1,3-Bis(1-butyl-3-carboxy-1,4-dihydro-4-oxo-7-quinolyloxy)-2-propanol | 10 | 71 | 85 |
| 1,3-Bis(3-carboxy-1,4-dihydro-1-methyl-4-oxo-7-quinolyloxy)-2-propanol | 5 | 62 | 69 |
| Cromoglycic Acid | 10 | 60 | 84 |
|  | 5 | 63 | 67 |

TABLE 2

Antiinflammatory Effect In the Carrageenin Test Upon i.v. and p.o. Application

| Compound | Dosage mg./kg. | Type of Application | % Inhibition |
|---|---|---|---|
| 1,3-Bis(1-ethoxy-3-carboxy-1,4-dihydro- | 10 | i.v. | 44 |
| 4-oxo-7-quinolyloxy)-2-propanol | 75 | p.o. | 28 |
| Cromoglycic Acid | 10 | i.v. | 10 |
|  | 75 | p.o. | 0 |

TABLE 3

Antibacterial Effect in Vitro
Minimum Inhibitory Concentration Measured in μg./ml.

| Against | 1,3-Bis(1-ethyl-3-carboxy-1,4-dihydro-4-oxo-7-quinolyloxy)-2-propanol | Cromoglycic Acid |
|---|---|---|
| Diplococcus pneumoniae | 50 | >100 |
| Staphylococcus aureus 30–8 | 12.5 | >100 |
| Staphylococcus aureus 30–3 | 12.5 | >100 |
| Staphylococcus aureus 30–2 | 25 | >100 |
| Staphylococcus aureus 30–64 | 50 | >100 |
| Staphylococcus aureus 30–107 | 50 | >100 |
| Staphylococcus aureus 30–109 | 25 | >100 |
| Staphylococcus aureus 30–53 | 50 | >100 |

Due to their pharmacological properties, the quinolonecarboxylic acid derivatives of this invention are suitable, in combination with vehicles and excipients conventional in galenic pharmacy, preferably for the treatment of inflammatory and allergic diseases of the respiratory tract, e.g., bronchial asthma or rhinitis.

The drug specialties are prepared in the usual way by converting the active agents, together with suitable additives, carriers, and flavor-ameliorating agents, into the desired forms of administration, e.g., tablets, dragees, capsules, solutions, or preferably inhalants.

For the production of inhalants, the quinolonecarboxylic acid derivatives are conventionally pulverized or dissolved or suspended in a suitable solvent and optionally combined with suitable additives, such as diluents, thickeners, suspension aids, propellant gases, flavor-ameliorating agents, etc. The active ingredients in the inhalants are customarily a quinolonecarboxylic acid derivative or a mixture of two quinolonecarboxylic acid derivatives; but it is also possible to formulate inhalants which contain, in addition to the quinolonecarboxylic acid derivatives of this invention, also other active agents, e.g., antibiotics, for example, chloramphenicol, tetracyclines, penicillins, cephalosporins, lincomycins, erythromycins, or rifomycins, or preferably also bronchodilators, for example, orciprenaline, isoetharine, or especially isoprenaline (as a salt, preferably as the sulfate).

It is furthermore likewise possible to dissolve or suspend the active ingredients in a physiologically compatible solvent, e.g., water or alcohol, and then optionally to combine this with the customary additives.

The thus-obtained solutions or suspensions which preferably contain 0.01–10% of active agent, can be applied with the aid of the customary inhalators, using analogous administration methods.

On the other hand, the active agents can be suspended or dissolved, optionally together with the usual additives, in a physiologically compatible propellant gas, e.g., "Freon". The thus-obtained suspensions or solutions can be dispensed in spray cans preferably equipped with a metering valve. The thus-produced inhalants, which preferably contain 0.01–10% of active agent, are also administered in the usual way.

For dry atomization, it is especially advantageous to impart to the active agents an average particle size of 0.01 to 10 μm, by means of micronizing or precipitation.

To increase the shelf life and to facilitate the aerosol formation, it is advantageous to furthermore add to these corticoid powders a solid, pharmacologically inert, water-soluble pulverulent carrier with an average particle size or 20–400 μm. Suitable carriers include, for example, dextran, mannitol, glucose and lactose. These powder-type inhalants, to which can also be added still other additives, e.g., flavor-ameliorating agents (e.g., saccharin) or bronchodilators (e.g., isoprenaline sulfate), customarily contain 0.1–30% of active agent. The production of powdery inhalants and their usage are described, for example, in British Patent No. 1,144,906.

The inhalants of this invention are utilized, as mentioned above, preferably for the treatment of allergic diseases of the respiratory tract, for example, rhinitic diseases, hay fever or bronchial asthma in mammals, including humans.

The quantity of inhalant to be applied per inhalation is varied in accordance with the graveness of the disease and the constitution of the patient being treated. Usually, about 0.1–100 mg, and preferably 1–50 mg, of quinolonecarboxylic acid derivative is applied per inhalation, optionally in combination with 0.01–10 mg of a bronchodilator.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

(A)
1-Butyl-1,4-dihydro-7-methoxy-4-quinolone-3-carboxylic Acid 11.0 g. (50 millimoles) of 4-hydroxy-7-methoxyquinoline-3-carboxylic acid is introduced into a suspension of 14.0 g. (351 millimoles) of pulverized sodium hydroxide in 200 ml. of dimethyl sulfoxide. The mixture is stirred for 10 minutes at room temperature, and then 16.1 ml. (150 mmol) of butyl bromide is added dropwise thereto so that the temperature does not exceed 25° C. Thereafter, the mixture is stirred for 2 hours at room temperature, poured into water, and acidified with hydrochloric acid. The thus-precipitated product is filtered off, washed with water, dried, and recrystallized from dimethylformamide.

Melting point: 160°–162° C. Yield: 9.18 g.

(B)
1-Butyl-1,4-dihydro-7-hydroxy-4-quinolone-3-carboxylic Acid 5.0 g. (18 mmol) of 1-butyl-1,4-dihydro-7-methoxy-4-quinolone-3-carboxylic acid is refluxed for 4 hours in 65 ml. of hydrobromid acid (48%). The mixture is then poured into water; the solid product is filtered off and recrystallized from dimethylformamide.

Melting point: 228°–240° C. Yield: 3.5 g.

(C)
1,4-DIHYDRO-7-HYDROXY-1-METHYL-4-QUINOLONE-3-CARBOXYLIC ACID 5.83 g. (25 mmol) of 1,4-dihydro-7-methoxy-1-methyl-4-quinolone-3-carboxylic acid is refluxed for 4 hours with 65 ml. of hydrobromic acid. The mixture is poured into water; the solid product is filtered off and recrystallized from acetic acid.

Melting point: 285°–293° C. Yield: 5.6 g.

(D) 1,3-BIS(3-NITROPHENOXY)-2-PROPANOL 44.3 g. (0.32 mole) of 3-nitrophenol is dissolved in 1.2 liter of isopropanol; 13.7 ml. of epichlorohydrin is added thereto and then a solution of 17.5 g. of potassium hydroxide in 250 ml. of isopropanol as well as 10 ml. of water are introduced. The mixture is refluxed for 48 hours, concentrated to half its volume, and combined with 250 ml. of water. The thus-precipitated product is filtered off, washed with water, and dried.

Melting point: 110° C. Yield: 24 g.

(E) 1,3-BIS(4-NITROPHENOXY)-2-PROPANOL 8.86 g. (63.7 mmol) of 4-nitrophenol is dissolved in 250 ml. of isopropanol; 2.75 ml. (35.1 mmol) of epichlorohydrin is added thereto, and thereafter a solution of 1.98 g. (35.3 mmol) of potassium hydroxide in 25 ml. of isopropanol as well as 1 ml. of water are introduced. The mixture is refluxed for 48 hours, concentrated to half its volume, and combined with 50 ml of water. The thus-precipitated product is filtered off and recrystallized from isopropanol/ethanol 1:1. Melting point: 144°–145° C. Yield: 6.4 g.

EXAMPLE 1

1,3-Bis(1-ethyl-3-carboxy-1,4-dihydro-4-oxo-7-quinolyloxy)-2-propanol (a) 0.46 g. (20 mmol) of sodium is introduced into 20 ml. of ethanol. After the reaction is completed, 2.33 g. (10 mmol) of 1-ethyl-1,4-dihydro-7-hydroxy-4-quinolone-3-carboxylic acid is dissolved in the thus-obtained sodium ethylate solution; thereafter, 0.91 ml. (11.7 mmol) of epichlorohydrin and a trace of potassium iodide are added to the reaction mixture. The latter is refluxed for 8 hours, evaporated, and the residue dissolved in water. The solution is extracted with chloroform and ethyl acetate and acidified to pH 5 with hydrochloric acid. The thus-precipitated product is filtered off, washed with water, dried, and dissolved in hot dimethylformamide. For purposes of crystallization, the product is combined with isopropyl ether. The resultant material is dried under vacuum at 100°.

Melting point: 305°–310° Yield: 1.26 g.

(b) 0.17 g (3.0 mmol) of pulverized potassium hydroxide is suspended in 5 ml. of dimethyl sulfoxide, and 0.10 g. (0.22 mmol) of 1,3-bis(3-carboxy-1,4-dihydro-4-oxo-7-quinolyloxy)-2-propanol is introduced. The mixture is stirred for 10 minutes at room temperature, then 0.17 ml. of diethyl sulfate is added dropwise. The mixture is agitated for 2 hours at room temperature, then introduced into water, and acidified. The thus-obtained solid product is filtered off, washed with water, extracted by boiling with acetic acid, and recrystallized from dimethylformamide/isopropyl ether.

Melting point: 305°-310° Yield: 0.05 g.

EXAMPLE 2

1,3-Bis(1-butyl-3-carboxy-1,4-dihydro-4-oxo-7-quinolyloxy)-2-propanol 0.096 g. (4.2 mmol) of sodium is introduced into 5 ml. of ethanol; then 0.56 g. (2.1 mmol) of 1-butyl-1,4-dihydro-7-hydroxy-4-quinolone-3-carboxylic acid, 0.19 ml. of epichlorohydrin, and a trace of potassium iodide are added thereto. The mixture is refluxed for 4 hours, and then the reaction mixture is made to dissolve completely with 2 N NaOH whereafter it is acidified with hydrochloric acid. The thus-precipitated product is filtered off, washed with water, and dried.

Melting point: 255°-260° Yield: 0.45 g.

EXAMPLE 3

1,3-Bis(3-carboxy-1,4-dihydro-1-methyl-4-oxo-7-quinolyloxy)-2-propanol 0.46 g. (20 mmol) of sodium is introduced into 20 ml. of methanol; then, 2.00 g. (9.1 mmol) of 1,4-dihydro-7-hydroxy-1-methyl-4-quinolone-3-carboxylic acid, 1.21 ml. (15.5 mmol) of epichlorohydrin, and a trace of potassium iodide are added thereto. The mixture is refluxed for 8 hours, evaporated, and the residue dissolved in water. The solution is extracted with chloroform and acidified with hydrochloric acid. The thus-precipitated product is filtered off, washed with water, and dried.

Melting point: 310° (decomposition). Yield: 0.82 g.

EXAMPLE 4

1,3-Bis(3-carboxy-1,4-dihydro-4-oxo-7-quinolyloxy)-2-propanol 10 g. (30 mmol) of 1,3-bis(3-nitrophenoxy)-2-propanol is dissolved in 250 ml. of methanol and hydrogenated in the presence of 1 g. of Pd-carbon (10%). The catalyst is filtered off, and the solution is evaporated; there remains 8.2 g. of crude 1,3-bis(3-aminophenoxy)-2-propanol. The latter is heated with 100 ml. of the diethyl ester of ethoxymethylenemalonic acid for 3 hours to 100°, then maintained for 1 hour at 100° under the vacuum of a water jet pump. The excess ethyl ester of ethoxymethylenemalonic acid is distilled off under vacuum. The residue is refluxed in 100 ml. of "Dowtherm A" for 30 minutes. After cooling, the mixture is combined with isopropyl ether. The thus-separated, crude 1,3-bis(3-ethoxycarbonyl-1,4-dihydro-4-oxo-7-quinolyloxy)-2-propanol is separated suspended in 150 ml. of 2 N NaOH, and refluxed for 2 hours. After cooling, the solution is extracted with ethyl acetate, acidified with hydrochloric acid, and combined with a small amount of methanol. The resultant crystalline material is filtered off, washed with water, and dried.

Melting point: >300°. Yield: 3.2 g.

EXAMPLE 5

1,3-Bis(3-carboxy-1,4-dihydro-4-oxo-6-quinolyloxy)-2-propanol 10 g. (30 mmol) of 1,3-bis(4-nitrophenoxy)-2-propanol is hydrogenated in methanol in the presence of 1.6 g. of Pd-carbon (10%). The catalyst is filtered off, and the filtrate is evaporated, leaving 13 g. of crude, oily 1,3-bis-(4-aminophenoxy)-2-propanol. This product is heated with 100 ml. of the diethyl ester of ethoxymethylenemalonic acid for 3 hours to 100°, then for 1 hour to 100° in a water jet pump vacuum. The excess diethyl ester of ethoxymethylenemalonic acid is distilled off under vacuum. The remainder is refluxed in 150 ml. of "Dowtherm A" for 30 minutes. After cooling, the solution is combined with isopropyl ether, and the thus-separated solid product is filtered off, thus obtaining 4 g. of crude 1,3-bis(3-carbethoxy-1,4-dihydro-4-oxo-6-quinolyloxy)-2-propanol, which is refluxed for 1 hour in 100 ml. of 2 N NaOH. After cooling, the mixture is extracted with ethyl acetate, and the aqueous phase is acidified with hydrochloric acid. The thus-produced oily compound is separated and stirred with ether until it has become solid. The solid product is filtered off, recrystallized from dimethylformamide, and dried under vacuum at 100°.

Melting point: >300°. Yield: 1.4 g.

EXAMPLE 6

1,3-Bis(1-ethyl-3-carboxy-1,4-dihydro-4-oxo-6-quinolyloxy)-2-propanol 1.5 g. (6.4 mmol) of 1-ethyl-1,4-dihydro-6-hydroxy-4-quinolone-3-carboxylic acid is introduced into a solution of 0.29 g. (12.6 mmol) of sodium in 15 ml. of ethanol; thereafter 0.58 ml. (7.5 mmol) of epichlorohydrin is added thereto, along with 20 mg. of potassium iodide. The mixture is refluxed for 4 hours, combined with 2 N NaOH until a clear solution is obtained, then acidified with 2 N HCl. The thus-precipitated product is filtered off, recrystallized from acetic acid, and dried under vacuum at 120°.

Melting point: >300°. Yield: 1.3 g.

EXAMPLE 7

1,3-Bis(1-ethyl-3-carboxy-1,4-dihydro-4-oxo-8-quinolyloxy)-2-propanol 0.466 g. (2 mmol) of 1-ethyl-1,4-dihydro-8-hydroxy-4-quinolone-3-carboxylic acid is suspended in 10 ml. of isopropanol; 0.086 ml. (1.1 mmol) of epichlorohydrin is added thereto, and then a solution of 0.224 g. (4.0 mmol) of potassium hydroxide in 5 ml. of isopropanol and 2 drops of water are furthermore introduced. The mixture is refluxed for 48 hours, combined with 2 N NaOH until a clear solution results, and then neutralized with 2 N HCl. The thus-precipitated material is filtered off, washed with water, and dried under vacuum.

Melting point: 250° (decomposition). Yield: 0.2 g.

EXAMPLE 8

2-Acetoxy-1,3-bis(1-ethyl-3-carboxyl-1,4-dihydro-4-oxo-7-quinolyloxy)-propane 1.0 g. (4.3 mmol) of 1,3-bis(1-ethyl-3-carboxy-1,4-dihydro-4-oxo-7-quinolyloxy)-2-propanol is heated in a mixture of 7.5 ml. of acetic anhydride and 7.5 ml. of acetic acid for 1 hour to 100°. The mixture is then poured into water, the thus-precipitated solid product is filtered off, washed with water, and dried under vacuum at 100°.

Melting point: 144°-147°. Yield: 1.0 g.

EXAMPLE 9

1,3-Bis(1-ethyl-3-carboxy-1,4-dihydro-4-oxo-7-quinolyloxy)-2-propanol, Disodium Salt 0.52 g. (1.0 mmol) of 1,3-bis(1-ethyl-3-carboxy-1,4-dihydro-4-oxo-7-quinolyloxy)-2-propanol is dissolved in a mixture of 2 ml. of 1 N NaOH solution and 20 ml. of methanol at room temperature. The mixture is then evaporated under vacuum and the residue recrystallized from water while decolorizing with activated carbon.

Melting point: 315° (decomposition). Yield: 0.39 g.

EXAMPLE 10

Composition of an Aerosol

| | |
|---|---|
| 1,3-Bis(1-ethyl-3-carboxy-1,4-dihydro-4-oxo-7-quinolyloxy)-2-propanol, disodium salt | 2.00% |
| Isoprenaline sulfate | 0.10% |
| Sodium dicetyl sulfosuccinate | 0.004% |
| Mixture (60:40) of Porpellant 12 and Propellant 14, to make up | 100.00% |

EXAMPLE 11

Composition of a Powder Formulation

| | |
|---|---|
| 1,3-Bis(1-ethyl-3-carboxy-1,4-dihydro-4-oxo-7-quinolyloxy)-2-propanol, disodium salt, micronized 2–8 μm | 20 mg. |
| Isoprenaline sulfate, micronized 2–8 μm | 0.1 mg. |
| Lactose, pulverized 80–120 μm | 15 mg. |

The values apply to one dosage unit.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A quinolone compound of the formula

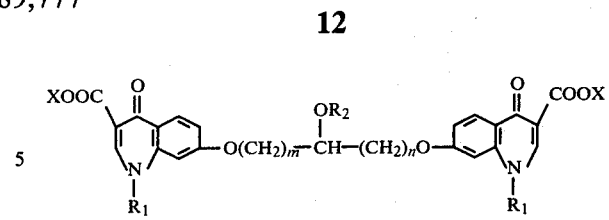

wherein
m and n independently are each 1–4;
$R_1$ is hydrogen or alkyl of 1–6 carbon atoms;
$R_2$ is hydrogen, alkanoyl of 1–8 carbon atoms or benzoyl; and
X is hydrogen or alkyl of 1–6 carbon atoms
or, for those compounds wherein X is H, the pharmaceutically acceptable salts thereof with a base.

2. A quinolone compound of claim 1, wherein m and n are each 1.

3. A quinolone compound of claim 1, wherein $R_2$ is hydrogen.

4. A quinolone compound of claim 1, wherein X is hydrogen, an alkali metal cation, an alkaline earth metal cation, ammonium, piperazinyl or N-methylglucamine.

5. 1,3-Bis(1-ethyl-3-carboxy-1,4-dihydro-4-oxo-7-quinolyloxy)-2-propanol, a compound of claim 1.

6. 1,3-Bis(1-butyl-3-carboxy-1,4-dihydro-4-oxo-7-quinolyloxy)-2-propanol, a compound of claim 1.

7. 1,3-Bis(3-carboxy-1,4-dihydro-1-methyl-4-oxo-7-quinolyloxy)-2-propanol, a compound of claim 1.

8. 1,3-Bis(3-carboxy-1,4-dihydro-4-oxo-7-quinolyloxy)-2-propanol, a compound of claim 1.

9. 2-Acetoxy-1,3-bis(1-ethyl-3-carboxy-1,4-dihydro-4-oxo-7-quinolyloxy)-propane, a compound of claim 1.

10. Disodium salt of 1,3-bis(1-ethyl-3-carboxy-1,4-dihydro-4-oxo-7-quinolyloxy)-2-propanol, a compound of claim 1.

11. A pharmaceutical composition comprising an amount of a compound of claim 1 effective to treat an allergic disease of the respiratory tract and a pharmaceutically acceptable carrier.

12. The pharmaceutical composition of claim 11 which is an inhalant.

13. The pharmaceutical composition of claim 12 comprising 0.01–10% of said effective compound.

14. The composition of claim 12 further comprising an additional ingredient which is a bronchodilator.

15. A method of treating an allergic disease of the respiratory tract in a mammal which comprises administering an amount of a compound of claim 1 effective for such treatment.

* * * * *